(12) United States Patent
Frank et al.

(10) Patent No.: US 10,125,076 B2
(45) Date of Patent: Nov. 13, 2018

(54) EXTRACTIVE DEHYDRATION PROCESS

(71) Applicant: Dow Global Technologies LLC, Midland, MI (US)

(72) Inventors: Timothy C. Frank, Midland, MI (US); Vishesh H. Shah, Midland, MI (US); Paul A. Larsen, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 31 days.

(21) Appl. No.: 15/323,532

(22) PCT Filed: Jun. 25, 2015

(86) PCT No.: PCT/US2015/037664
§ 371 (c)(1),
(2) Date: Jan. 3, 2017

(87) PCT Pub. No.: WO2016/007306
PCT Pub. Date: Jan. 14, 2016

(65) Prior Publication Data
US 2017/0144956 A1    May 25, 2017

Related U.S. Application Data

(60) Provisional application No. 62/021,243, filed on Jul. 7, 2014.

(51) Int. Cl.
*C07C 51/42* (2006.01)
*C07C 51/487* (2006.01)
*C07C 51/377* (2006.01)

(52) U.S. Cl.
CPC .......... *C07C 51/487* (2013.01); *C07C 51/377* (2013.01)

(58) Field of Classification Search
USPC ........................................................ 562/531
See application file for complete search history.

(56) References Cited

U.S. PATENT DOCUMENTS

| | | | | |
|---|---|---|---|---|
| 3,968,153 A | * | 7/1976 | Ohrui | B01D 11/0492 203/15 |
| 2010/0168472 A1 | * | 7/2010 | Bogan, Jr. | C07C 45/52 562/532 |

FOREIGN PATENT DOCUMENTS

| | | |
|---|---|---|
| JP | 2010180171 A | 8/2010 |
| WO | 2002074402 A1 | 9/2002 |

OTHER PUBLICATIONS

Li, et al.; Extraction of Glyoxylic Acid, Glycolic Acid, Acrylic Acid, and Benzoic Acid With Trialkylphosphine Oxyide; Journal Chemical Engineering Data, vol. 48, pp. 621-624, 2003.
Bauer, W.; Acrylic Acid and Derivatives, Kirk-Othmer Encyclopedia of Chemical Technology, vol. 1, pp. 342-369, 2003.

* cited by examiner

*Primary Examiner* — Ana Z Muresan
(74) *Attorney, Agent, or Firm* — Edward L. Brant

(57) ABSTRACT

A process comprising subjecting a composition comprising an alpha- or beta-hydroxycarboxylic acid, water, an extraction solvent, and an acid catalyst to extractive dehydration to form an unsaturated carboxylic acid product.

9 Claims, No Drawings

EXTRACTIVE DEHYDRATION PROCESS

BACKGROUND OF THE INVENTION

The invention relates to a process for the preparation of a hydroxycarboxylic acid via extractive dehydration.

There is much interest in producing various compounds from biorenewable sources. For example, lactic acid, also called 2-hydroxypropionic acid, can be prepared by fermenting sugar, followed by recovering lactic acid from the fermentation broth using distillation or extraction. Distillation methods for recovery of lactic acid from aqueous broth are described in WO 2002/074402. Much has been published regarding use of extractants such as trioctylamines or phosphine oxides to recover hydrophilic carboxylic acids from aqueous solutions. An example is the article by Li, Wang, Li, and Dai, "Extraction of Glyoxylic Acid, Glycolic Acid, Acrylic Acid, and Benzoic Acid with Trialkylphosphine Oxide," J. Chem. Eng. Data, vol. 48, pp. 621-624 (2003). Conventional methods for extracting acrylic acid from water are described by William Bauer, Jr. in "Kirk-Othmer Encyclopedia of Chemical Technology," Vol. 1, pp. 342-369 (2003).

Acrylic acid is a very high volume commodity chemical. It can be produced by the oxidation of propylene or propane. However, it would be desirable to be able to economically manufacture acrylic acid from biorenewable resources. Acrylic acid can be prepared from 3-hydroxypropionic acid (3HP). It is known that 3HP can be prepared from renewable resources, such as sugars. Conventional methods call for recovering 3HP from an aqueous solution and then passing the 3HP through a vapor-phase dehydration reactor to convert the 3HP to acrylic acid. However, this requires recovering 3HP directly from aqueous solution, which is difficult and expensive to accomplish, as 3HP, like other hydroxycarboxylic acids such as lactic acid and glycolic acid, is relatively hydrophilic, making it difficult to extract from an aqueous solution or a fermentation broth.

Producing an unsaturated carboxylic acid from biorenewable sources is a complex process requiring multiple unit operations. None of the approaches of the prior art combine chemical dehydration of a hydroxycarboxylic acid compound with simultaneous extraction of the reaction product. It would be desirable to have a simple process for making and recovering acrylic acid and other unsaturated carboxylic acids.

SUMMARY OF THE INVENTION

The invention is such a process comprising: (a) providing a dispersion comprising an extraction solvent, an acid catalyst, water and an alpha- or beta-hydroxycarboxylic acid and/or a salt thereof, wherein the dispersion comprises an organic phase and an aqueous phase, (b) dehydrating the hydroxycarboxylic acid to form the corresponding unsaturated carboxylic acid product, while simultaneously extracting the product into the organic phase, (c) separating the phases, and (d) recovering the product from the organic phase.

Surprisingly, the reaction to form an unsaturated carboxylic acid product from the corresponding hydroxycarboxylic acid can be conducted while simultaneously extracting the product from the reaction mixture.

DETAILED DESCRIPTION OF THE INVENTION

The process of the invention employs an acid catalyst, an extraction solvent and an aqueous solution comprising a hydroxycarboxylic acid and/or a salt thereof.

As used herein, "a," "an," "the," "at least one," and "one or more" are used interchangeably. The terms "comprises," "includes," and variations thereof do not have a limiting meaning where these terms appear in the description and claims. Thus, for example, dehydration of "a" hydroxycarboxylic acid to form "a" corresponding unsaturated carboxylic acid product can be interpreted to mean dehydration of "one or more" hydroxycarboxylic acids to form "one or more" corresponding unsaturated carboxylic acid products.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the use of the term "hydrophobic solvent" means that the solubility of the solvent in water is less than 5% by weight and the solubility of water in the solvent is less than 5% by weight, measured at 25° C.

As used herein, the use of the term "(meth)" followed by another term such as acrylate refers to both acrylates and methacrylates. For example, the term "(meth)acrylate" refers to either acrylate or methacrylate; the term "(meth)acrylic" refers to either acrylic or methacrylic; and the term "(meth)acrylic acid" refers to either acrylic acid or methacrylic acid.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

In one embodiment of the invention, wherein the hydroxycarboxylic acid is 3HP, the invention provides an efficient way of converting aqueous 3HP via dehydration to acrylic acid within a fermentation broth and simultaneously selectively extracting the acrylic acid into an extraction solvent away from most of the water and the various impurities present in the broth, including, e.g., cell debris, proteins, residual sugars, and inorganic salts such as ammonium sulfate. The acrylic acid can then be isolated from the solvent phase, e.g., via standard distillation methods. For the purposes of the invention, the term "simultaneously," when used in connection with the dehydration reaction and extraction of the reaction product, means that at some point the extraction and the dehydration reaction are both occurring at the same time. As will be recognized by those skilled in the art, at the start of the reaction there will be very little to no extraction occurring. The rate of extraction will increase as more product becomes available in the reaction mixture.

The invention overcomes well-known difficulties that arise using conventional extraction or distillation methods to first recover the highly hydrophilic 3HP from water and in a subsequent step converting the 3HP to acrylic acid product.

The process of the invention converts the 3HP to acrylic acid within the aqueous broth and then, as soon as acrylic acid is formed, selectively extracts the acrylic acid product into an organic solvent phase. This approach also advantageously minimizes undesirable polymerization and degradation of the product. The process of the invention advantageously is practiced with reaction and extraction conducted simultaneously in a single unit operation (termed extractive dehydration or reactive extraction). The invention allows independent adjustment of process variables including temperatures, hydroxy acid concentrations, catalyst, and residence time of each liquid phase in order to provide process flexibility for the conversion of 3HP to acrylic acid, and the extraction of acrylic acid product into the solvent phase.

Examples of the starting alpha- or beta-hydroxycarboxylic acid include 3-hydroxypropionic acid, lactic acid, 3-hydroxybutyric acid, 3-hydroxy-2-methylpropionic acid or 2-hydroxy-2-methylpropionic acid. Preferably, the alpha- or beta-hydroxycarboxylic acid is a beta-hydroxycarboxylic acid. Most preferably, the beta-hydroxycarboxylic acid is 3HP. Salts of the starting hydroxycarboxylic acid may be employed as the starting hydroxycarboxylic acid. Mixtures of the starting hydroxycarboxylic acid, including salts thereof, may be employed. The alpha- or beta-hydroxycarboxylic acid may be derived from microbial or plant cells that contain or produce alpha- or beta-hydroxycarboxylic acids.

In one embodiment of the invention, the starting hydroxycarboxylic acid is provided in a fermentation broth. Fermentation processes to produce hydroxycarboxylic acids, and salts thereof, are well known to those skilled in the art. In one embodiment of the invention, an aqueous microbial fermentation is conducted to produce the ammonium salt of a hydroxycarboxylic acid in a fermentation broth.

The broth may be pre-treated prior to reaction to remove biomass, e.g., via centrifugation and or microfiltration or another method, to adjust pH, and/or to concentrate the broth by removing water such as, for example, via evaporation or by permeation of water through a membrane. Thus, the broth may be provided to the process as a clarified broth. In one embodiment of the invention, the broth is not pre-treated.

In one embodiment of the invention, the pre-treated broth is processed to convert a hydroxycarboxylic acid to the corresponding unsaturated carboxylic acid via chemical dehydration using a homogeneous or heterogeneous acid catalyst.

The process employs an acid catalyst for the dehydration of a hydroxycarboxylic acid to the corresponding unsaturated carboxylic acid. Acid catalysts are well known to those skilled in the art. The acid catalyst can be employed in solution form or as a solid catalyst. Examples of solid acid catalysts include sulfonated ion exchange media, various alumina and zeolite materials, NAFION catalysts, and the like. Examples of other suitable catalytic acids include sulfuric acid, hydrochloric acid, methanesulfonic acid, and p-toluenesulfonic acid. Mixtures of acid catalysts can be employed. The acid is employed in a catalytic amount. Advantageously, the acid concentration in the reaction liquid in the reaction zone is such that the pH of the liquid is 2 or less.

The extraction solvent is the solvent employed in the recovery of the unsaturated carboxylic acid from the reaction medium. Advantageously, the solvent is a nonaqueous, hydrophobic solvent with the right properties for both the extraction of unsaturated carboxylic acid from the reaction mixture and for the subsequent removal of unsaturated carboxylic acid from the solvent. For example, the solvent must be suitable for selectively extracting unsaturated carboxylic acid from the reaction medium, leaving the initial hydroxycarboxylic acid in the aqueous phase. Advantageously, the solvent is a nonaqueous, hydrophobic solvent having a partition ratio of at least 0.1 where the partition ratio is defined as the wt % of unsaturated carboxylic acid in the solvent divided by the wt % of unsaturated carboxylic acid in the aqueous phase at equilibrium at 25° C. Examples of suitable solvents include hydrophobic ketones, nitromethane, nitroethane, and chlorinated solvents such as dichloroethane, dichloromethane, and perchloroethylene. Chlorinated solvents are preferred, and 1,2-dichloroethane is most preferred. Mixtures of solvents can be employed.

The solvent is employed in an amount sufficient to allow the recovery of unsaturated carboxylic acid from the reaction medium and to allow for the subsequent removal of unsaturated carboxylic acid from the solvent. Advantageously, the weight ratio of solvent to aqueous feed to the reaction zone is from 10:1 to 1:10, preferably from 7:1 to 2:1.

In one embodiment of the invention, water is the medium for the biological reaction, e.g., fermentation, that produces the hydroxycarboxylic acid. In one embodiment of the invention, sufficient water for the process of the invention is provided by the fermentation broth or other source of hydroxycarboxylic acid. However, if desired, additional water may be added to the reaction vessel. In various embodiments of the invention, the amount of water present at the start of the dehydration reaction is from 30 to 98, 50 to 90, or 60 to 80 weight percent of the total weight of water and hydroxycarboxylic acid present.

Polymerization inhibitors optionally can be added to the process to minimize yield loss due to polymerization of acrylic acid. A plethora of polymerization inhibitors, and methods of using them, are known to those skilled in the art. Examples of inhibitors include hydroquinone, the monomethyl ether of hydroquinone (MEHQ), 4-hydroxy-2,2,6,6-tetramethylpiperidine 1-oxyl (4HT) and phenothiazine. Mixtures of inhibitors can be employed. The inhibitor can be a mixture of fugitive inhibitors and captive inhibitors, such as those disclosed in EP 2 683 748.

The hydroxycarboxylic acid is processed under reactive extraction conditions in a reaction mixture, which comprises the hydroxycarboxylic acid, the catalyst, water and the solvent, such that a major portion of the hydroxycarboxylic acid is converted via a dehydration reaction to the corresponding unsaturated carboxylic acid. The extraction of the unsaturated carboxylic acid proceeds when there is unsaturated carboxylic acid in the reaction mixture.

In one embodiment of the invention, an extraction solvent is added to the aqueous broth during the course of the reaction of the hydroxycarboxylic acid, e.g., 3HP, to unsaturated carboxylic acid product, e.g., acrylic acid, such that a portion of the acrylic acid product is extracted into the organic solvent phase and away from the majority of water and organic impurities present in the aqueous phase, e.g., fermentation broth.

The temperature in the reaction zone advantageously is from 100 to 250° C. In various embodiments of the invention, the temperature is from 125 to 200° C., or from 150 to 180° C. Residence times within the reaction zone can range from the order of seconds to hours. For example, the residence time can be from 5 seconds to 1 hour or more, from 10 seconds to 30 minutes, or from 20 seconds to 10 minutes. The residence time is not particularly critical. Longer residence times allow high conversion to acrylic acid. Additional residence time also allows a reduction in the required reaction temperature and/or the acid concentration. However, additional residence time may also allow for unwanted side reactions to take place, such as polymerization of acrylic acid or degradation of acrylic acid. Thus, the residence time and temperature employed are largely a matter of choice for the process operator.

The process can be designed using the organic phase or the aqueous phase as the dispersed phase or continuous phase. This choice will depend on many factors, primarily including the type of equipment employed, and process operating conditions, as is known to those skilled in the art.

The process pressure is not particularly critical. In one embodiment of the invention, the selected pressure is close to the total vapor pressure exerted by the extraction solvent and the water at the average temperature of the reaction zone. For example, a temperature of 150° C. corresponds to a water vapor pressure of 55 psig, a temperature of 180° C. corresponds to a water vapor pressure of 130 psig, and a temperature of 200° C. corresponds to a water vapor pressure of 210 psig. The presence of strong acid will suppress the vapor pressure. The vapor pressure of the solvent will also have an impact on the pressure in the reaction zone. In various embodiments of the invention, the average absolute pressure in the reaction zone is from 0.2 bar to 30 bar, from 0.5 to 20 bar, or from 0.8 to 15 bar.

Extractive dehydration combines chemical dehydration of the hydroxycarboxylic acid, e.g., 3HP, to unsaturated carboxylic acid product, e.g., acrylic acid with the ability to selectively extract the product out of the aqueous phase, away from the reaction zone and away from water. In addition to serving as an efficient way of isolating the unsaturated carboxylic acid product, in-situ extraction of the unsaturated carboxylic acid from the reaction zone advantageously can help drive conversion in cases where the dehydration reaction becomes limited by chemical equilibrium.

For example, the hydroxycarboxylic acid, e.g., 3HP, is not extracted into the solvent to any great extent. The extraction factor is much larger for transfer of acrylic acid into the solvent phase. Thus, the 3HP substantially stays in the reaction zone until it is converted to acrylic acid.

Co-extraction of other carboxylic acids may occur, but proteins, sugars, and other hydrophilic impurities advantageously remain in the aqueous raffinate. If whole broth is used, the process advantageously is operated in such a manner that at least 50 wt % of the biomass stays with the aqueous phase. The amount of biomass that stays with the aqueous phase will vary depending on the type of biomass employed.

One reaction zone effluent stream primarily comprises the unsaturated carboxylic acid product and the solvent. Following the extraction of the unsaturated carboxylic acid from the reaction zone, this effluent stream is separated into a stream that primarily comprises the unsaturated carboxylic acid and another stream that primarily comprises the solvent. The separation of the unsaturated carboxylic acid from the solvent can be accomplished using methods well known to those skilled in the art, such as distillation.

The process may be conducted in a continuous, semi-batch or batch manner. In one embodiment of the invention, the process is continuous, which advantageously minimizes contact time of the solvent and unsaturated carboxylic acid at reaction conditions in order to minimize the potential for unwanted side reactions, including polymerization, and/or decomposition.

Any suitable equipment can be employed. Those skilled in the art will readily be able to design suitable equipment using appropriate materials of construction. For example, the reaction vessel can be a stirred tank reactor associated with a decanter. Liquid/liquid extraction vessels, e.g., static extraction columns such as packed or trayed columns or towers can be employed for a continuous process. Mechanically agitated extraction columns such as, for example, reciprocating-plate extractors or rotating impeller extractors, can be employed. Centrifugal extractors can also advantageously be employed in view of their short residence time.

The alpha, beta-unsaturated carboxylic acid product formed by the process of the invention is a compound of formula (I)

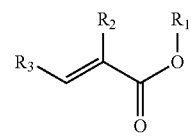

wherein $R_1$ is H or $C_1$-$C_8$ alkyl, $R_2$ is H or $C_1$-$C_4$ alkyl, and $R_3$ is H, methyl or ethyl.

The $C_1$-$C_4$ alkyl moiety can be a branched or unbranched carbon moiety such as, for example, methyl, ethyl, propyl, isopropyl, butyl, tert-butyl, sec-butyl or isobutyl.

The $C_1$-$C_8$ alkyl moiety for the purposes of the invention can be a branched or unbranched alkyl moiety such as, for example, methyl, ethyl, isopropyl, n-propyl, n-butyl, isobutyl, sec-butyl, 2-ethylbutyl, 1,3-dimethylbutyl, tert-butyl, isopentyl, 1-methylpentyl, n-pentyl, n-hexyl, 1-methylhexyl, 2-ethylhexyl or isoheptyl.

Acrylic acid is the preferred alpha, beta-unsaturated carboxylic acid. The carboxylic acid product can be employed for a wide variety of known uses. For example, unsaturated carboxylic acids, especially acrylic acid, can be employed in applications such as the preparation of superabsorbent polymers, latexes, adhesives, etc.

SPECIFIC EMBODIMENTS OF THE INVENTION

The following examples are given to illustrate the invention and should not be construed as limiting its scope.

EXAMPLE 1—Batch Experiment in a Stirred Vessel

An aqueous bacterial fermentation broth containing ammonium-3-hydroxypropionate (A3HP) is filtered using microfiltration membranes (commercially obtainable from Amafilter GmbH) to remove cell debris and related bio-mass solids to yield 100 mL of clarified aqueous solution. The aqueous solution is added to a vented vessel containing an impeller for mixing the contents. Sufficient concentrated aqueous phosphoric acid (85% by weight) is added to the solution to adjust the pH to 2, converting the dissolved ammonium-3-hydroxypropionate to 3-hydroxypropionic acid (3HP) and ammonia, some of which leaves the vessel through the vent. The resulting solution contains 0.1 wt % residual glucose, 0.5 wt % proteinaceous matter, and 5 wt % 3HP. 1000 mL of 1,2-dichloroethane and 20 mL of concentrated phosphoric acid (85 wt %) are mixed with the aqueous solution in the vessel and the contents are then heated to 120° C. and held for 45 minutes at a pressure corresponding to the vapor pressure of the solution, which is not measured as it is not a critical process control parameter. After 45 minutes, the heating is turned off and the aqueous solution is allowed to cool for one hour with agitation. The agitation is then stopped and the contents are allowed to settle into two liquid layers at room temperature. The top aqueous layer contains proteinaceous matter, residual sugar, and related compounds, plus 1 to 2 grams of acrylic acid. The lower solvent layer contains also contains 1 to 2 grams of the acrylic acid product. A minor portion of the acrylic acid forms acrylic oligomers. The solvent is then drained from the vessel and distilled to yield acrylic acid as a bottoms product with a purity of 90 wt %. Further distillations are performed to increase the purity of the acrylic acid product to 99.5 wt %.

A gradient liquid chromatography (LC) method is used to determine concentrations of 3HP, acrylic acid, and oligomers. Samples are neutralized to pH 2-4 prior to analysis at 30° C. The LC system is an Agilent 1200 unit with Atlas 8.2 data acquisition. It includes a vacuum degasser, low-pressure mix quaternary pump, autosampler, and variable UV detector. The analysis is done using a Waters T3 column (3 micron, 4.6×150 mm), 5 microliter sample size, and 210 nm UV detection. Mobile phase A is 0.1 wt % phosphoric acid in water. Mobile phase B is 0.1 wt % phosphoric acid in acetonitrile. The total mobile phase flow rate is 1 mL/min. The mobile phase composition is programmed as follows (in terms of vol. % B): 0%, 45%, 90%, 0%, and 0% at 0, 3, 15, 17, and 25 minutes, respectively. External standard calculation is used for quantitation.

EXAMPLE 2—Continuous Experiment in a Static Extraction Column

1000 L of clarified aqueous solution is prepared from fermentation broth as in Example 1. The solution is added to a vented vessel containing an impeller for mixing the contents. Concentrated aqueous phosphoric acid (85% by weight) is added to the solution at a ratio of 20 parts aqueous acid for every 100 parts aqueous feed by volume. The phosphoric acid converts the dissolved A3HP to 3HP and volatile ammonia, at least 30 wt % of which leaves the vessel through the vent. Excess phosphoric acid is present to serve as a dehydration catalyst.

The resulting aqueous solution is continuously pumped to a pilot scale static extraction column at a rate of 100 mL/min using a Milton Roy positive displacement metering pump. The extraction column is 3.5 inches in diameter and is packed with ¼ in ceramic Intalox saddles. The column is constructed from Hastelloy C and is about 7 ft tall with a 6 ft packed section extending from the top and leaving a 1 ft non-packed section at the bottom. The aqueous feed is fed to the bottom of the packed section of the column, about 1 ft from the bottom. 1,2-Dichloroethane solvent is fed to the top of the column at a rate of 1 L/min using a second Milton Roy positive displacement metering pump. The injected solvent breaks up into droplets that pass down the column through the aqueous phase that fills the column. The column is jacketed to control the temperature within the column at 120 to 130° C. The column is designed to operate at the vapor pressure of the liquid-liquid mixture, which is above atmospheric pressure. The average residence time of aqueous liquid in the column is between 45 minutes and 2 hours. The bottom 1 ft section of the column below the packed section serves to allow the dispersed solvent droplets to coalesce into a layer of solvent at the bottom. The interface between the aqueous phase and the coalesced solvent layer at the bottom is maintained at a location between 3 inches and 6 inches from the bottom of the column by periodically drawing off the bottom of the column through a discharge valve to control the liquid-liquid interface level. The solvent leaving the bottom of the column is cooled below 60° C. as it leaves the column by passing it through a water-cooled tubing coil. The cooled solvent contains a majority of the acrylic acid product produced by the reaction. It is distilled to recover the acrylic acid product from the solvent.

What is claimed is:

1. A process comprising (a) providing a dispersion comprising an extraction solvent, an acid catalyst, water and an alpha- or beta-hydroxycarboxylic acid and/or a salt thereof, wherein the dispersion comprises an organic phase and an aqueous phase, (b) dehydrating the hydroxycarboxylic acid to form the corresponding unsaturated carboxylic acid product, while simultaneously extracting the product into the organic phase, (c) separating the phases, and (d) recovering the product from the organic phase; wherein the extraction solvent is a chlorinated organic solvent.

2. The process of claim 1 wherein the alpha- or beta-hydroxycarboxylic acid and/or a salt thereof are, respectively 3-hydroxy propionic acid and ammonium-3-hydroxypropionate.

3. The process of claim 1 wherein the unsaturated carboxylic acid product is acrylic acid.

4. The process of claim 1 wherein the solvent is 1,2-dichloroethane.

5. The process of claim 1 wherein steps (b), and (c) are done in the same piece of equipment.

6. The process of claim 1 wherein steps (b) and (c) are conducted in a static extraction column, a mechanically-agitated extraction column, or a stirred-tank reactor.

7. The process of claim 1 wherein steps (b) and (c) are conducted in a centrifugal extractor.

8. The process of claim 1 wherein the alpha- or beta-hydroxycarboxylic acid and/or a salt thereof is derived from a renewable biological source material.

9. The process of claim 1 wherein the aqueous phase of the dispersion comprises from 30 to 98 weight percent water, based on the weight of the aqueous phase.

* * * * *